(12) United States Patent
Schultz

(10) Patent No.: US 8,460,237 B2
(45) Date of Patent: Jun. 11, 2013

(54) MEDICAL DEVICE CONTROL HANDLE WITH MULTIPLYING LINEAR MOTION

(75) Inventor: Jeffrey W. Schultz, Chino, CA (US)

(73) Assignee: Biosense Webster (Israel), Ltd., Yokneam (IL)

( * ) Notice: Subject to any disclaimer, the term of this patent is extended or adjusted under 35 U.S.C. 154(b) by 0 days.

(21) Appl. No.: 13/293,909

(22) Filed: Nov. 10, 2011

(65) Prior Publication Data
US 2013/0123691 A1    May 16, 2013

(51) Int. Cl.
*A61M 31/00* (2006.01)
(52) U.S. Cl.
USPC .......................................... 604/95.04; 604/528
(58) Field of Classification Search
USPC .................... 604/95.01, 95.04, 528
See application file for complete search history.

(56) References Cited

U.S. PATENT DOCUMENTS

| | | |
|---|---|---|
| RE34,502 E | 1/1994 | Webster, Jr. |
| 5,275,151 A | 1/1994 | Shockey et al. |
| 5,415,158 A | 5/1995 | Barthel et al. |
| 5,667,476 A | 9/1997 | Frassica et al. |
| 5,904,667 A | 5/1999 | Falwell |
| 6,123,699 A | 9/2000 | Webster, Jr. |
| 6,171,277 B1 | 1/2001 | Ponzi |
| 6,183,463 B1 | 2/2001 | Webster, Jr. |
| 6,485,455 B1 | 11/2002 | Thompson et al. |
| 7,122,020 B2 * | 10/2006 | Mogul ...................... 604/95.04 |
| 2010/0069834 A1 | 3/2010 | Schultz |
| 2011/0054287 A1 | 3/2011 | Schultz |
| 2011/0054446 A1 | 3/2011 | Schultz |

FOREIGN PATENT DOCUMENTS

EP     0 904 796 A2    3/1999

OTHER PUBLICATIONS

EPO Extended European Search Report dated Jan. 30, 2013 for EP Application No. 12192276.9, 5 pgs.

* cited by examiner

*Primary Examiner* — Laura Bouchelle
(74) *Attorney, Agent, or Firm* — Christie, Parker & Hale, LLP

(57) ABSTRACT

A catheter adapted for use in a tubular region of the heart, has a catheter body, a deflectable intermediate section and a distal a mapping assembly that has a generally circular portion adapted to sit on or in a tubular region of the heart. A control handle of the catheter allows for deflection of the catheter via a first and second puller wire responsive to a deflection assembly and manipulation of distal assembly via a third puller wire responsive to a linear motion actuator assembly. The linear motion actuator assembly includes a pair of user interface knobs, a body to which a proximal end of the third puller wire anchored, and a pair of arms that movably suspends the body and transmits longitudinal travel of the knobs to the body in a manner that multiples the travel of the body relative to the travel of the knobs.

17 Claims, 13 Drawing Sheets

MEDICAL DEVICE CONTROL HANDLE WITH MULTIPLYING LINEAR MOTION

FIELD OF INVENTION

This invention relates to a control handle for medical devices, in particular, a control handle having a mechanism for multiplying linear motion of a tensile member in manipulating a medical device.

BACKGROUND

Electrode catheters have been in common use in medical practice for many years. They are used to stimulate and map electrical activity in the heart and to ablate sites of aberrant electrical activity. Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. Prior to treating the condition, one has to first determine the location of the wavelets. Various techniques have been proposed for making such a determination, including the use of catheters with a mapping assembly that is adapted to measure activity within a pulmonary vein, coronary sinus or other tubular structure about the inner circumference of the structure. One such mapping assembly has a tubular structure comprising a generally circular main region generally transverse and distal to the catheter body and having an outer circumference and a generally straight distal region distal to the main region. The tubular structure comprises a non-conductive cover over at least the main region of the mapping assembly. A support member having shape-memory is disposed within at least the main region of the mapping assembly. A plurality of electrode pairs, each comprising two ring electrodes, are carried by the generally circular main region of the mapping assembly.

In use, the electrode catheter is inserted into a guiding sheath which has been positioned a major vein or artery, e.g., femoral artery, and guided into a chamber of the heart. Within the chamber, the catheter is extended past a distal end of the guiding sheath to expose the mapping assembly. The catheter is maneuvered through movements that include deflection of a distal portion of the catheter so that the mapping assembly is positioned at the tubular region in the heart chamber. The ability to control the exact position and orientation of the catheter and also the configuration of the mapping assembly is critical and largely determines how useful the catheter is.

Steerable catheters are generally well-known. For example, U.S. Pat. No. Re 34,502 describes a catheter having a control handle comprising a housing having a piston chamber at its distal end. A piston is mounted in the piston chamber and is afforded lengthwise movement. The proximal end of the elongated catheter body is attached to the piston. A puller wire is attached to the housing and extends through the piston, through the catheter body, and into a tip section at the distal end of the catheter body. The distal end of the puller wire is anchored in the tip section of the catheter. In this arrangement, lengthwise movement of the piston relative to the housing results in deflection of the catheter tip section.

The design described in U.S. Pat. No. RE 34,502 is generally limited to a catheter having a single puller wire. If bi-directional deflection is desire, more than one puller wire becomes necessary. Moreover, if more control is desired, such as contraction of the mapping assembly, an additional puller wire is needed. Furthermore, it is desirable that the mechanism for actuating the additional puller wire provide more "throw," that is, a greater degree of travel in the puller wire in relation to the travel of the actuating mechanism itself. Control handles providing greater throw are known, including those described in U.S. application Ser. No. 12/550,307, filed Aug. 28, 2009, entitled CATHETER WITH MULTI-FUNCTIONAL CONTROL HANDLE HAVING ROTATIONAL MECHANISM and U.S. application Ser. No. 12/550,204, filed Aug. 28, 2009, entitled CATHETER WITH MULTI-FUNCTIONAL HANDLE HAVING LINEAR MECHANISM, the entire disclosures of which are hereby incorporated by reference. These control handles convert linear motion to rotational motion. Accordingly, a need exists for a control handle capable of moving a puller wire with multiplied linear motion.

SUMMARY OF THE INVENTION

The present invention is directed to a medical device control handle with a distal component which is adjustable by a puller member responsive to actuators of a linear motion actuator assembly in the control handle, wherein the control handle provides a multiplying mechanism by which linear travel of the puller member is increased relative to the linear travel of the actuators. The resulting increase in "throw" of the control member is desirable as it allows for greater degree in adjustability of the distal component, especially where space is limited inside a control handle. As medical devices, especially, electrophysiology catheters, become more complex with more components to actuate, a control handle should provide control of multiple puller members without significantly expanding the size of the control handle.

In one embodiment, a control handle has an actuator assembly and a housing configured with first and second incline cam portions to act on the actuator assembly. The actuator assembly includes a body to which a proximal end of a puller member is fixed, first and second knobs, and first and second arms, wherein the arms are adapted to suspend the body within the control handle and transfer longitudinal movement of the first and second knobs to the body in a manner that multiplies the travel distance of the body and hence the puller member relative to the travel distance of the knobs.

In a more detailed embodiment, the arms at opposing ends are movably coupled to the knobs and the body, respectively such that the incline cams of the housing can act on the arms to vary the angle of attachment of the arms to the knobs and the body so that the travel distance of the body can be greater than the travel distance of the knobs.

In a more detailed embodiment, an outer end of the arms is coupled to a finger that extends radially from each knob and into the control handle housing and the travel distance of the body can be varied by changing the angle at which the finger extends from the knob relative to the control handle housing. In an alternate embodiment, the travel distance of the body can be doubled by the use of a pulley on the body so that the puller member is wound approximately 180 degrees about the pulley with its proximal end anchored distally of the body.

In another embodiment of the present invention, a catheter includes an elongated body, a distal assembly having an adjustable configuration and a control handle having an actuator assembly which acts on a puller member that extends through the elongated body and the distal assembly. A housing of the control handle is configured with first and second opposing incline cam portions to jointly act on opposing user interface knobs of the actuator assembly mounted on the control handle. The actuator assembly includes a body to which a proximal end of the puller member is fixed, and first and second arms, wherein the arms are adapted to suspend the body within the control handle and transfer longitudinal movement of the first and second knobs to the body in a manner that multiplies the travel distance of the body and hence the puller member relative to the travel distance of the knobs.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

DETAILED DESCRIPTION OF THE INVENTION

The present invention is directed to a control handle 10 with a multiplying linear motion actuator assembly for actuating a puller wire to provide greater "throw" or degree of travel of the puller wire in manipulating or adjusting a component distal of the control handle. The control handle may be used with any variety of medical devices, for example, an electrophysiology (EP) catheter configured for mapping and/or ablation of tissue, including the heart, an embodiment of which is illustrated in FIG. 1.

Figure 1:
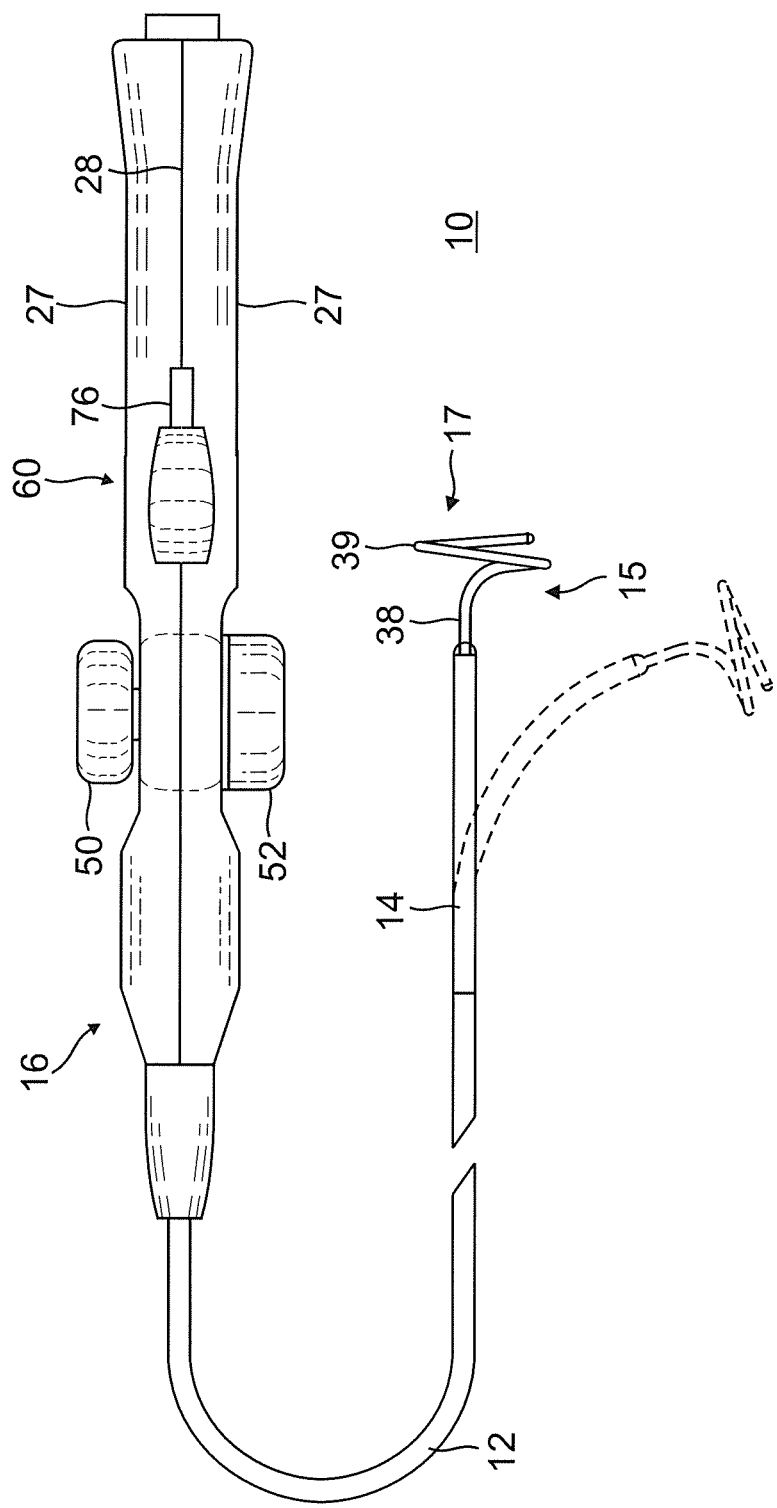
FIG. 1 is a top plan view of one embodiment of the catheter of the present invention.

The catheter of FIG. 1 comprises an elongated catheter body 12, a deflectable intermediate section 14 at a distal end of the catheter body 12, and a tip section 15 including a distal assembly 17 having, for example, a helical foam, at a distal end of the intermediate section 14. A control handle 16 for use with the catheter has a deflection dial 50 that is configured to actuate a pair of puller wires extending from the control handle 16 and through the catheter body 12 and intermediate section 14 for bi-directional deflection of the intermediate section. In accordance with a feature of the present invention, the control handle further includes a multiplying linear motion assembly having a pair of opposing linear knobs for actuating a third puller wire in manipulating or adjusting the distal assembly 17, for example, to contract the helical form of the distal assembly.

Figure 2A:
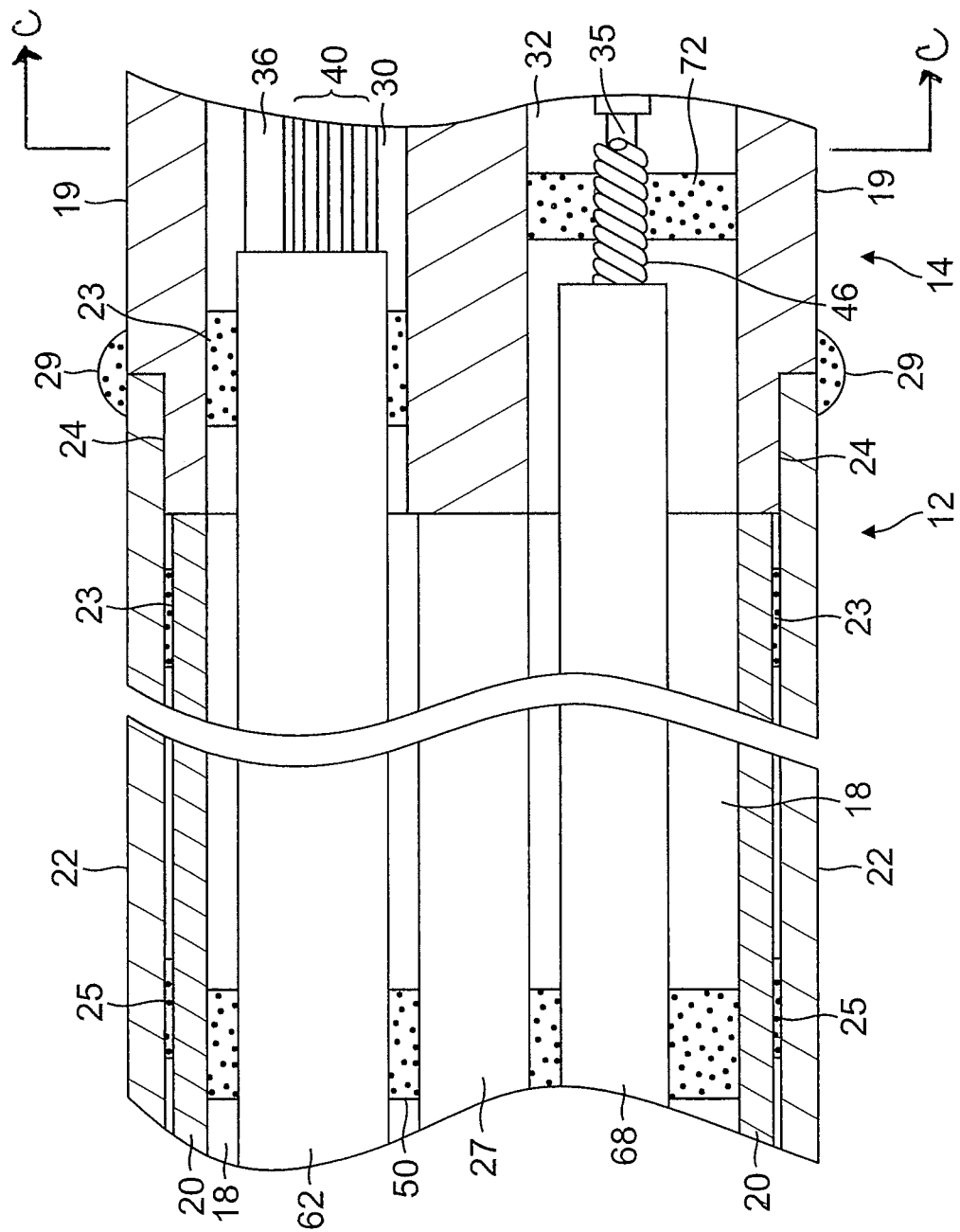
FIG. 2A is a side cross-sectional view of an embodiment of a junction of a catheter body and an intermediate section, taken along a first diameter.
Figure 2B:
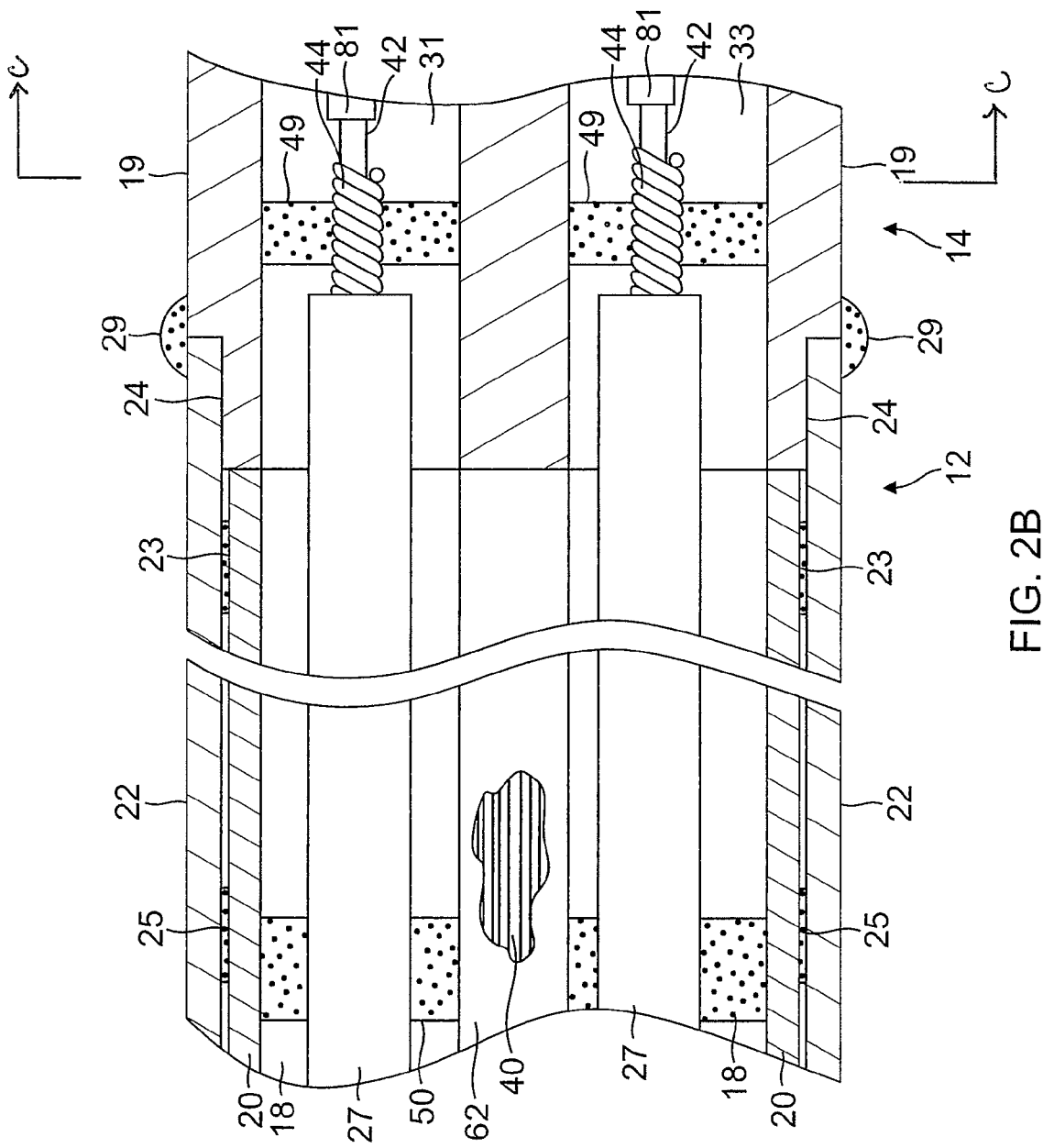
FIG. 2B is a side cross-sectional view of the junction of FIG. 2A, taken along a second diameter generally perpendicular to the first diameter.

With reference to FIGS. 2A and 2B, the catheter body 12 comprises a single, central or axial lumen 18. The catheter body 12 is flexible, i.e., bendable, but substantially non-compressible along its length. The catheter body 12 may be of any suitable construction and made of any suitable material. In one embodiment, the catheter body 12 comprises an outer wall 22 made of a polyurethane or nylon. The outer wall 22 comprises an imbedded braided mesh of stainless steel or the like to increase torsional stiffness of the catheter body 12 so that, when the control handle 16 is rotated, the tip section of the catheter 10 will rotate in a corresponding manner.

The outer diameter of the catheter body 12 is not critical, but is preferably no more than about 8 French. Likewise the thickness of the outer wall 22 is not critical. The inner surface of the outer wall 22 is lined with a stiffening tube 20, which can be made of any suitable material, preferably polyimide. The stiffening tube 20 is held in place relative to the outer wall 22 at the proximal end of the catheter body 12. A first glue joint 23 is made between the distal ends of the stiffening tube 20 and the outer wall 22 by a fast drying glue, e.g. Super Glue®. Thereafter, a second glue joint 25 is formed between the proximal ends of the stiffening tube 20 and outer wall 22 using a slower drying but stronger glue, e.g., polyurethane.

The stiffening tube 20, along with the braided outer wall 22, provides improved torsional stability while at the same time minimizing the wall thickness of the catheter, thus maximizing the diameter of the single lumen. The outer diameter of the stiffening tube 20 is about the same as or slightly smaller than the inner diameter of the outer wall 22. Polyimide tubing is suitable because it may be very thin walled while still providing very good stiffness. This maximizes the diameter of the central lumen 18 without sacrificing strength and stiffness. Polyimide material is typically not used for stiffening tubes because of its tendency to kink when bent. However, it has been found that, in combination with an outer wall 22 of polyurethane, nylon or other similar material, particularly having a stainless steel braided mesh, the tendency for the polyimide stiffening tube 20 to kink when bent is essentially eliminated with respect to the applications for which the catheter is used.

In one embodiment, the outer wall 22 has an outer diameter of about 0.092 inch and an inner diameter of about 0.063 inch and the polyimide stiffening tube 20 has an outer diameter of about 0.0615 inch and an inner diameter of about 0.052 inch.

Figure 2C:
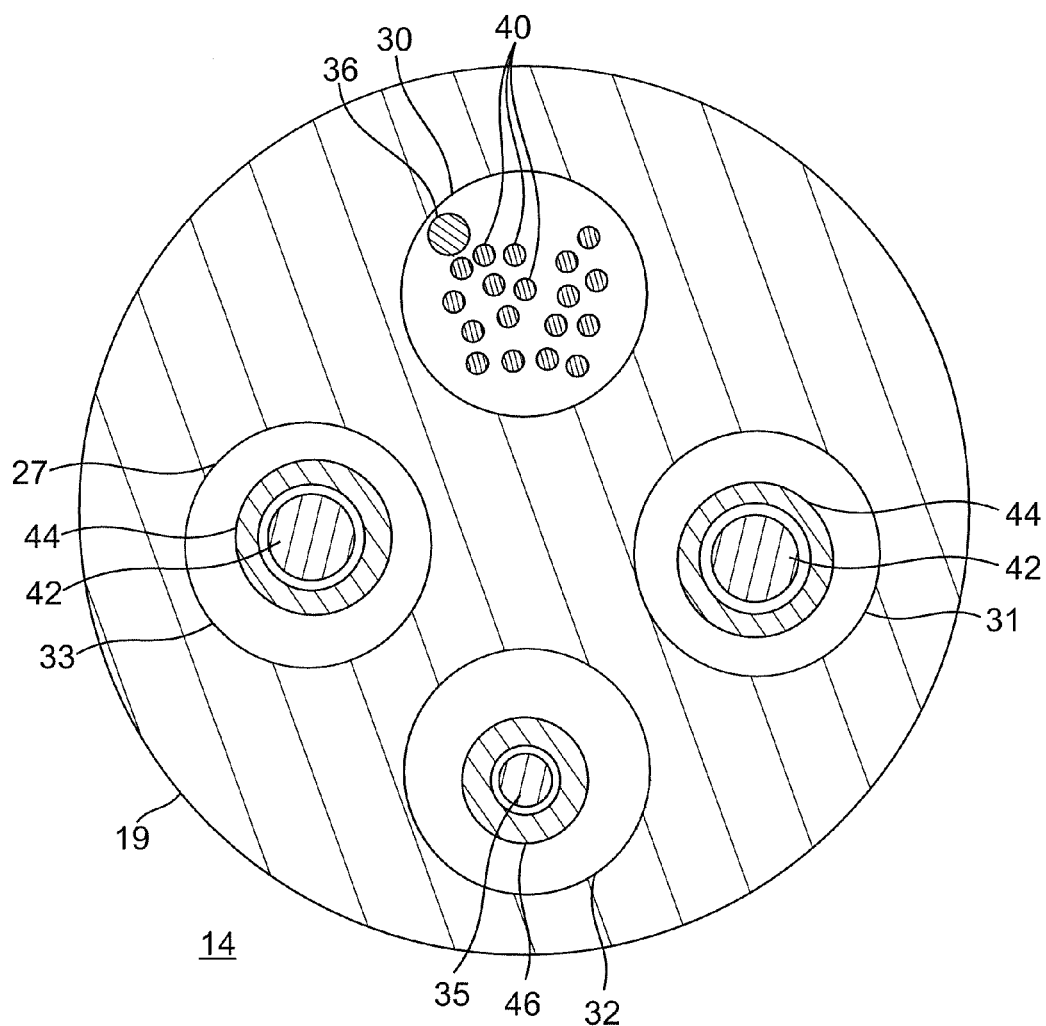
FIG. 2C is an end cross-sectional view of the intermediate section of FIGS. 2A and 2B, taken along line C-C.

As shown in FIGS. 2A, 2B and 2C, the intermediate section 14 comprises a shorter section of tubing 19 with multiple lumens, for example, first, second, third and fourth lumens 30, 31, 32 and 33. The tubing 19 is made of a suitable non-toxic material which is preferably more flexible than the catheter body 12. A suitable material for the tubing 19 is braided polyurethane, i.e., polyurethane with an embedded mesh of braided stainless steel or the like. The outer diameter of the intermediate section 14, like that of the catheter body 12, is preferably no greater than about 8 French. The size of the lumens is not critical. In one embodiment, the intermediate section has an outer diameter of about 7 French (0.092 inch) and the lumens are generally about the same size, having a diameter of about 0.022 inch, or selected lumens can have a slightly larger diameter of about 0.036 inch.

A means for attaching the catheter body 12 to the intermediate section 14 is illustrated in FIGS. 2A and 2B. The proximal end of the intermediate section 14 comprises an inner counter bore 24 that receives the outer surface of the polyimide stiffener 20. The intermediate section 14 and catheter body 12 are attached by glue 29 or the like.

As shown in FIGS. 2A and 2B, extending through the single lumen 18 of the catheter body 12 are various components, for example, lead wires and multiple puller wires, and any other wires or cables. Longitudinal movement of the puller wires relative to the catheter body 12 enables user control of various parts of the catheter via the control handle. In one embodiment, there are a pair of deflection puller wires 42 for deflecting the intermediate section 14 and a contraction puller wire 35 for adjusting the distal assembly 17 of the tip section 15.

A single lumen catheter body 12 may be preferred over a multi-lumen body because the single lumen 18 body can permit better tip control when rotating the catheter 10. The single lumen 18 permits the components passing therethrough to float freely within the catheter body. If such components were restricted within multiple lumens, they can build up energy when the handle 16 is rotated, resulting in the catheter body 12 having a tendency to rotate back if, for example, the handle is released, or if bent around a curve, to flip over, either for which are undesirable performance characteristics.

One deflection puller wire 42 extends through the central lumen 18 of the catheter body 12 and into the second lumen 31 of the intermediate section 14. Another deflection puller wire 42 extends through the central lumen 18 and into the fourth lumen 33 of the intermediate section 14.

In that regard, the lumens 31, 33 should be off-axis and diametrically opposed to each other for bi-directional deflection in a plane. The distal ends of the deflection puller wires 42 are anchored to the wall of the tubing 19 near the distal end of the intermediate section 14 by means of T-anchors (not shown) as understood by one of ordinary skill in the art. In the intermediate section 14, each deflection puller wires 42 extends through a plastic, e.g. Teflon®, sheath 81, which prevents the deflection puller wires 42 from cutting into the wall of the tubing 19 of the intermediate section 14 when the intermediate section 14 is deflected.

As shown in FIG. 2B, compression coils 44 in surrounding relation to the deflection puller wires 42 extend from the proximal end of the catheter body 12 to the proximal end of the intermediate section 14. The compression coils 44 are made of any suitable metal, e.g., stainless steel. The compression coils 44 are tightly wound on itself to provide flexibility, i.e., bending, but to resist compression. The inner diameter of the compression coils 44 is preferably slightly larger than the diameter of the puller wires 42. For example, when a puller wire 42 has a diameter of about 0.007 inches, the compression coil 44 preferably has an inner diameter of about 0.008 inches. The Teflon® coating on the puller wire 42 allows them to slide freely within the compression coils 44. The outer surface of the compression coils 44 is covered by a flexible, non-conductive sheath 27 to prevent contact between the compression coils 44 and other components, such as lead wires and cables, etc. In one embodiment, a non-conductive sheath is made of polyimide tubing.

The compression coils 44 are anchored at their proximal ends to the proximal end of the stiffening tube 20 in the catheter body 12 by glue joint 50 (FIG. 2B) and at its distal end near the proximal end of the intermediate section 14 in the second lumen 31 and fourth lumen 33 by glue joints 49 (FIG. 2B).

With reference to FIG. 1, at the distal end of the intermediate section 14 is the mapping assembly 17. The mapping assembly 17 comprises a generally straight proximal region 38 and a generally circular main region 39. The proximal region 38 is mounted on the intermediate section 14 and the generally circular main region carries a plurality of electrodes for mapping and/or ablation.

In the disclosed embodiment, the contraction puller wire 35 is provided to contract the generally circular main region 39 to thereby change or reduce its diameter, for example, when mapping or ablating circular or tubular regions of the heart. The contraction wire 35 has a proximal end anchored in the control handle 16 as described further below. As illustrated in FIG. 2A, the contraction wire 35 extends through the central lumen 18 of the catheter body 12, through the third lumen 32 of the intermediate section 14 and into the distal assembly 17.

A third compression coil 46 is situated within the catheter body 12 and intermediate section shaft 14 in surrounding relation to the contraction wire 35 (FIG. 2A). The third compression coil 46 extends from the proximal end of the catheter body 12 and to near the distal end of the third lumen 32 of the intermediate section 14. The third compression coil 46 is made of any suitable metal, such as stainless steel, and is tightly wound on itself to provide flexibility, i.e., bending, but to resist compression. The inner diameter of the third compression coil 46 is preferably slightly larger than the diameter of the contraction wire 35. The outer surface of the compression coil 46 is covered by a flexible, non-conductive sheath 68, e.g., made of polyimide tubing. The third compression coil 46 preferably is formed of a wire having a square or rectangular cross-sectional area, which makes it less compressible than a compression coil formed from a wire having a circular cross-sectional area. As a result, the third compression coil 46 keeps the catheter body 12, and particularly the intermediate section 14, from deflecting when the contraction wire 35 is manipulated to contract the distal assembly 17 as it absorbs more of the compression.

The third compression coil 46 is anchored at its proximal end to the stiffening tube 20 of the catheter body 12 by the proximal glue joint 50 and to the intermediate section 14 by distal glue joint 73.

It is understood that glue joints throughout the catheter 10 may comprise polyurethane glue or the like. The glue may be applied by means of a syringe or the like through a hole made in the tubing walls. Such a hole may be formed, for example, by a needle or the like that punctures the tubing walls where the needle is heated sufficiently to form a permanent hole. The glue is then introduced through the hole to wick around the component(s) within the tubing to form a glue joint about the entire circumference of the component(s).

The lead wires 40 attached to the ring electrodes on the distal assembly 17 extend through the first lumen 30 of the intermediate section 14 (FIG. 2A), through the central lumen 18 of the catheter body 12, through the control handle 16, and terminate at their proximal end in a connector (not shown) which is connected to an appropriate monitor or other device for receiving and displaying the information received from the ring electrodes. The portion of the lead wires 40 extending through the central lumen 18 of the catheter body 12, control handle 16 and proximal end of the intermediate section 14 is enclosed within a protective sheath 62, which can be made of any suitable material, preferably polyimide.

An electromagnetic position sensor (not shown) is mounted in or near the distal assembly 17. A sensor cable 36 extends from the sensor into the lumen 30 of the intermediate section (along with the electrode lead wires 40), into the central lumen 18 of the catheter body 12 and into the control handle where it terminates in a suitable connector (not shown).

With reference to FIG. 1, the control handle 16 comprises a generally elongated handle housing 27, which can be made of any suitable rigid material, such as plastic configured through a suitable molding process. In the illustrated embodiment, the housing includes two opposing halves 16a and 16b that generally mirror each other and are joined by glue, sonic welding or other suitable means along a longitudinal peripheral seam 28 around the housing.

Figure 3:
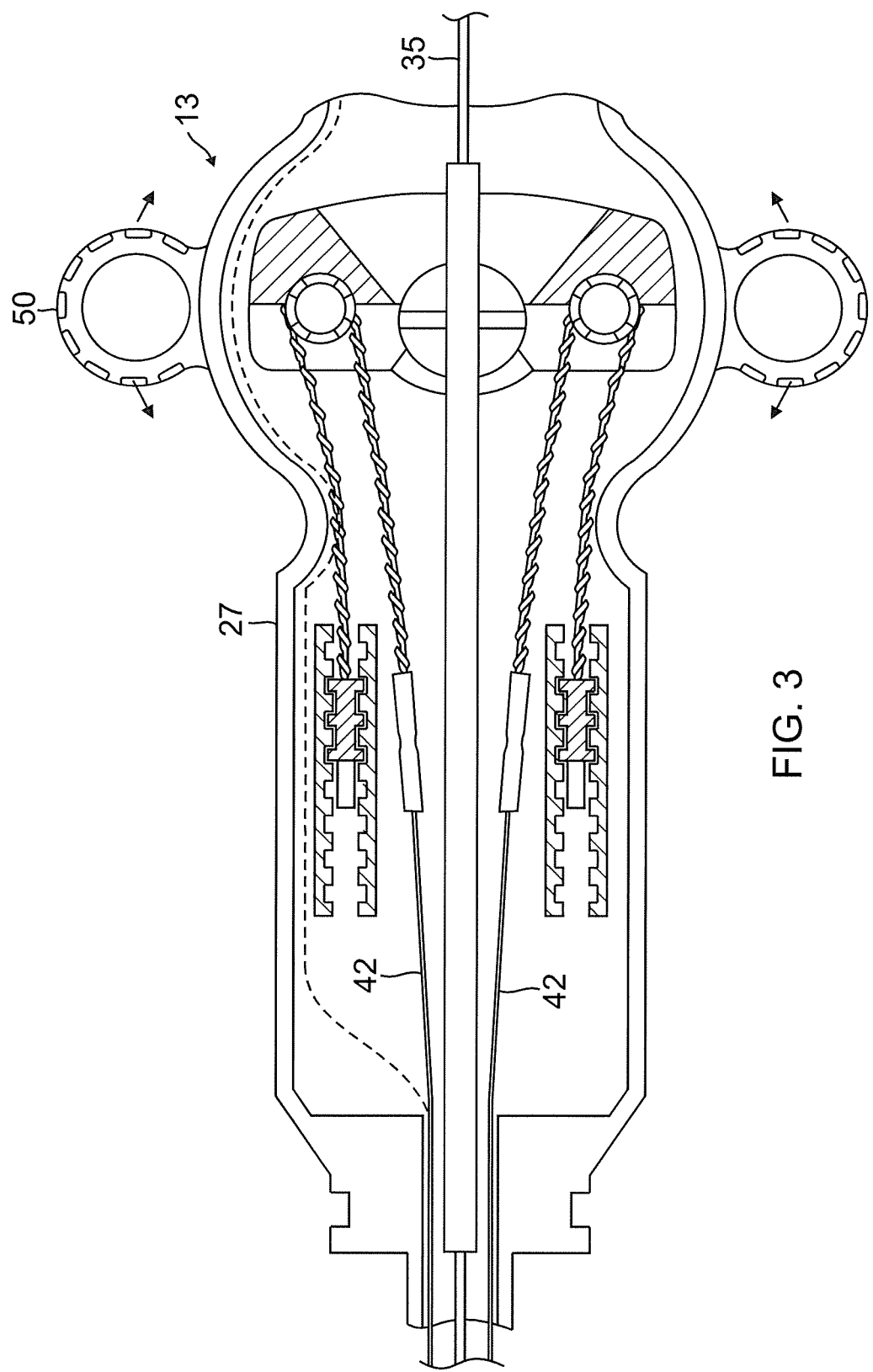
FIG. 3 is a top plan view of an embodiment of a control handle housing half.

In the illustrated embodiment of FIG. 1, the control handle 16 houses components of a deflection control assembly 13 that includes the deflection dial 50 for bi-directional deflection of the intermediate section 14 via the first and second puller wires 42. As illustrated in FIG. 3, by rocking the deflection dial 50 in one direction, the puller wire in that direction is drawn proximally to deflect the intermediate section in that direction.

Each puller wire 42 is made of any suitable metal, such as stainless steel or Nitinol. Preferably each puller wire has a low friction coating, such as a coating of Teflon® or the like. Each puller wire has a diameter preferably ranging from about 0.006 inch to about 0.012 inch. Preferably both of the puller wires have the same diameter. Flat puller wires may be used in place of round puller wires. Their cross sectional dimensions should be such that they provide comparable tensile strengths as round puller wires. Alternatively, tensile fibers can be used in whole or in part. They may be of a high modulus fiber material, preferably having an ultimate tensile strength substantially in the range of 412-463 ksi (2480-3200 Mpa) such as High Molecular Density Polyethylene (e.g., Spectra™ or Dyneema™), a spun para-aramid fiber polymer (e.g., Kevlar™) or a melt spun liquid crystal polymer fiber rope (e.g., Vectran™), or a high strength ceramic fiber (e.g., Nextel™). The term fiber is used herein interchangeably with the term fibers in that the tensile fiber may be of a woven or braided construction. In any case, these materials tend to be flexible, providing suitable durability when used in wrapped engagement with the pulleys and the like for greater throw in deflecting the catheter tip. Further, they are substantially non-stretching, which increases the responsiveness to the manipulation of the control handle, and nonmagnetic so that they generally appear transparent to an MRI. The low density of the material causes it to be generally transparent to an x-ray machine. The materials can also be nonconductive to avoid shorting. Vectran™, for example, has high strength, high abrasion resistance, is an electrical insulator, nonmagnetic, is polymeric, and has low elongation under sustained loading conditions.

A suitable deflection assembly with a deflection dial is described in co-pending U.S. application Ser. No. 12/211,728, filed Sep. 16, 2008, entitled CATHETER WITH ADJUSTABLE DEFLECTION SENSITIVITY, the entire disclosure of which is hereby incorporated by reference. Suitable deflection control handles and parts thereof are described in U.S. patent application Ser. No. 08/924,611, filed Sep. 5, 1997, entitled "Omni-Directional Steerable Catheter", Ser. No. 09/130,359, filed Aug. 7, 1998, entitled "Bi-Directional Control Handle for Steerable Catheter", and Ser. No. 09/143,426, filed Aug. 28, 1998, entitled "Bidirectional Steerable Catheter with Bidirectional Control Handle", the entire disclosures of which are hereby incorporated by reference.

For adjusting the distal assembly 17 by means of a third puller wire, e.g., the contraction wire 35, a proximal end of the contraction wire is anchored in the control handle 16 for actuation by the multiplying linear motion assembly 60 housed in the control handle 16. In the disclosed embodiment, the linear motion assembly 60 is proximal of the deflection assembly in the control handle.

Figure 4:
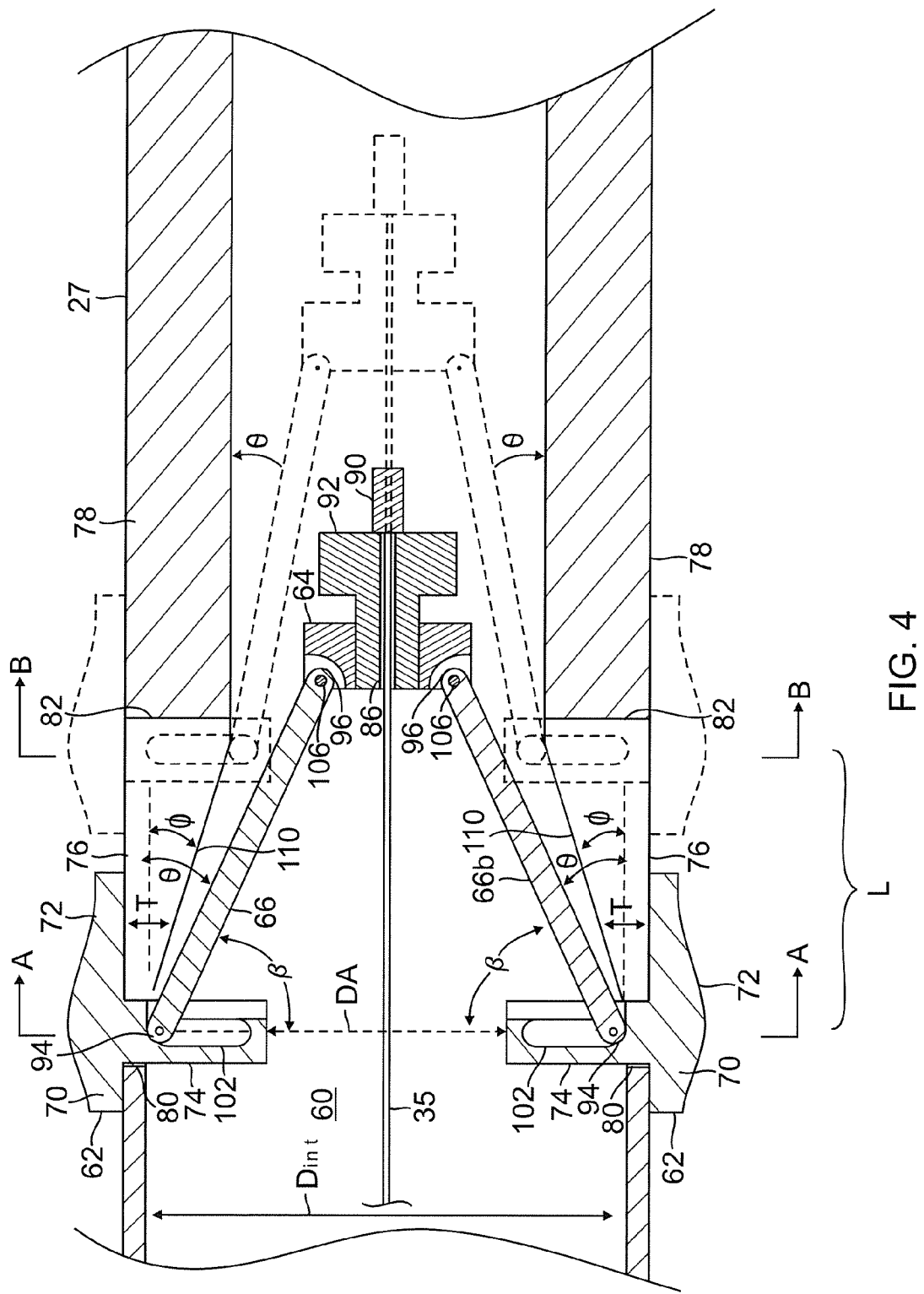
FIG. 4 is a side cross-sectional view of an embodiment of a linear motion actuator assembly provided in a control handle.

As illustrated in the embodiment of FIG. 4, the linear motion assembly 60 includes first and second linear actuators or control knobs 62, a puller wire anchor 64, and first and second rigid arms 66 extending therebetween to link movement of the knobs to the anchor. Because the anchor 64 is connected to the control knobs 62 via the rigid arms 66, it is understood that longitudinal translational movement of the knobs results in longitudinal translation movement of the anchor in actuating the third puller wire 35. In accordance with a feature of the present invention, the arms are movably connected to the knobs and the anchor so that at least the angle of attachment, if not also the position of attachment, of the arms can vary to increase (or "multiply") the travel of the anchor relative to the travel of the control knobs.

The first and second control knobs 62 are diametrically located at opposing sides of the housing 27 along a diametrical axis DA of the control handle 16. Each knob has an outer interface portion 70 with a surface area 72 for contact with the user's hand. Each knob also has an elongated inner portion or finger 74 that extends into the interior of the control handle housing through a respective axial slot 76. The slot has a predetermined length formed in opposing locations in the housing. The knobs 62 are therefore slidable longitudinally by a user along an outer surface 78 of the control handle for the distance L between an end 80 (e.g., a distal end in FIGS. 4 and 5) and another end 82 (e.g., a proximal end in FIGS. 4 and 5) of each axial slot 76. The significance of which is explained further below, thickness T of the housing halves at the slots 76 varies and tapers from a maximum thickness to a minimum thickness.

The fingers 74 extend at an angle β relative to the housing 16, ranging between about 0 and 90 degrees, preferably between about 40 and 60 degrees. In the embodiment of FIG. 4, the angle β is about 90 degrees. It is understood that although the knobs are illustrated as two separate members, they can be connected at their adjacent ends or have a single, continuous construction, where the fingers 74 are connected and extend across the interior of the housing. Such a connection secures the knobs to the housing and ensures synchronous movement of the knobs.

The puller wire anchor 64 has a structure sized for longitudinal movement within the interior of the control handle housing. In the illustrated embodiment, it has a body with a longitudinal tunnel or channel 86 through which the third puller wire 35 extends. The third puller wire is anchored thereto, for example, by a ferrule 90 crimped to the wire's proximal end. It is understood that tension in the third puller wire is adjustable by any suitable means, for example, a tension adjusting insert 92 that can interlock with the anchor 64 at various longitudinal positions to provide the appropriate tension on the third puller wire.

Each of the first and second arms 66 is of a generally rigid structure, having a length R between an outer end 94 and an inner end 96. The outer end 94 is attached to a respective knob 62. The inner end 96 is attached to the anchor 64 generally at a joint location. And, because the length R is greater than half of the interior diameter $D_{int}$ of the control handle housing, the arms 66 advantageously suspend the anchor 64 longitudinally offset a distance from the diametrical axis DA along the central longitudinal axis of the control handle 16. In the illustrated embodiment of FIG. 4, the puller wire anchor 64 is suspended to the right (or proximal) of the knobs 62.

Figure 4A:
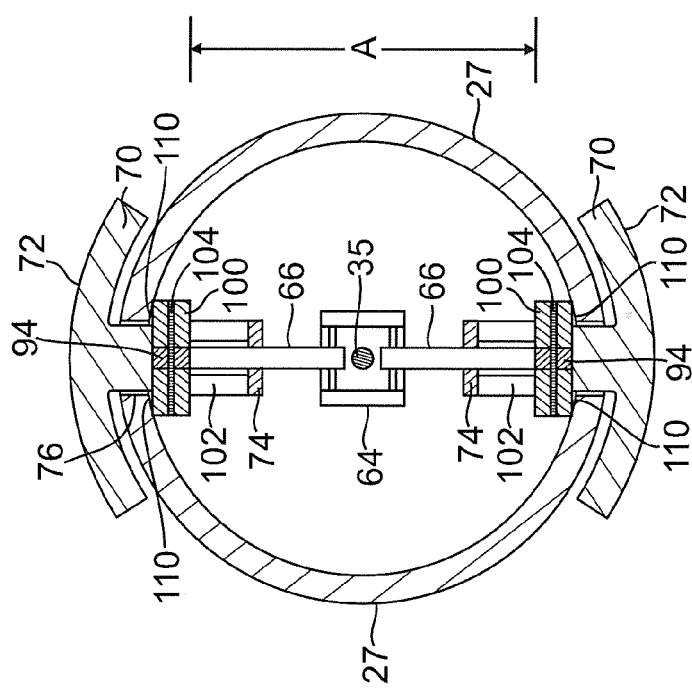
FIG. 4A is an end cross-sectional view of the linear motion actuator assembly of FIG. 4, taken along line A-A.
Figure 4B:
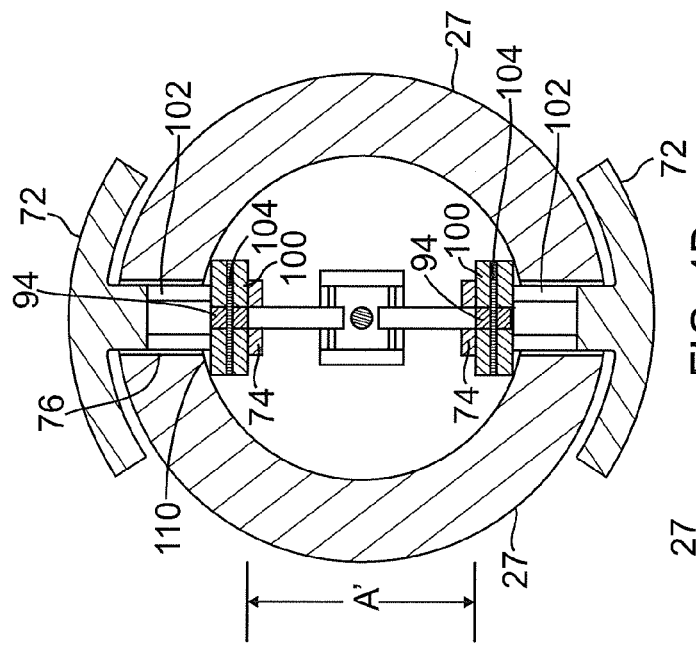
FIG. 4B is an end cross-sectional view of the linear motion actuator assembly of FIG. 4, taken along line B-B.

In the embodiment of FIGS. 4, 4A and 4B, to movably couple a knob 62 and the respective arm 66 in a manner that allows for increased or multiplication of travel of the puller wire anchor 64 relative to the knobs 62, at least one roller 100, if not a pair, is provided at each outer end 94 of each arm 66. Each roller extends transversely from the arm, e.g., at about 90 degrees, and is received in slot 102 formed in the fingers 74 of the knobs 62. Each roller is rotatable about its respective pin 104. Each slot 102 is aligned with its finger 74. An angle θ defines the angle between the arm 66 and the control handle housing 27.

The rollers 100 provide at least both a translational connection and a pivotal connection between the outer ends 94 of the arms 66 and their respective knobs 62. In particular, each roller 100 translates in its slot 102 while rotating (or pivoting, used interchangeably herein) about pin 104 to allow the angle θ of the arm 66 to vary.

Figure 5:
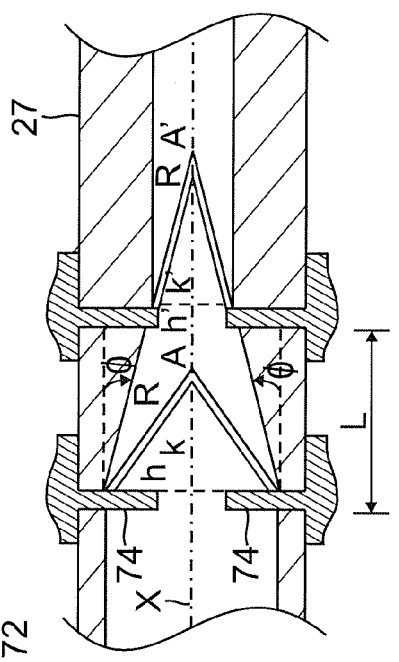
FIG. 5 is a schematic representation of the linear motion actuator assembly of FIG. 4.

As the outer ends 94 of the arm translates and rotates relative to the housing 27, the inner ends 96 also rotate about pins 106 relative to the anchor 64. As illustrated in FIG. 5, it is this variable attachment of the outer ends 94 and inner ends 96 of the arms 66, respectively, that allows the anchor 64 to "swing" for a greater distance k' when the knobs 62 are moved by the lesser distance k.

To actuate the arms 66 for the combined translation and pivotal movement relative to the control handle housing 27, a portion of the handle housing surrounding and defining each axial slot 76 is formed with a cam portion, for example, an incline 110, with which a respective roller 100 is in contact. The incline is oriented longitudinally along the control handle housing 27 with so that the rollers are guided by the axial slots 76 to ride on the incline 110.

The thickness of the control handle housing surrounding the slots 76 varies between a minimum at one end and a maximum at the other end. In the disclosed embodiment of FIG. 4, a minimum thickness is further from the anchor 64 (e.g., toward the distal end of the housing 27) and a maximum thickness is closer to the anchor (e.g., toward the proximal end of the housing 27). Thus, in the embodiment of FIG. 4, as the knobs 62 are actuated from the left to the right, that is, from the minimum thickness (with a maximum separation between opposing inner walls of the housing halves 27) to the maximum thickness (with a minimum separation between the opposing inner walls of the housing halves 27) of the incline 110, the position and angle of the arms 66 change relative to the housing 27 as the rollers 100 move along the incline 110. And, as the rollers approach each other (with the separation distance between the rollers 100 decreasing), the outer ends 94 of the rigid arms 66 move toward each other swinging out the anchor 64 to provide a greater offset distance k' between the anchor 64 and the diametrical axis DA. With the greater offset distance k', the third puller wire 35 correspondingly travels the greater offset distance for greater throw in control handle actuation of the distal assembly 17.

It is therefore understood that by sliding the knobs 62 along the incline 110 from the minimum thickness to the maximum thickness, the arms 66 are forced in a linear motion longitudinally along the control handle. As the rollers 100 (embodying the variable points of attachment between the arms 66 and the fingers 74) move along the incline, the separation distance between the rollers varies. In accordance with a feature of the present invention, a decreasing separation distance between the rollers 100 from distance A (FIG. 4A) to distance A' (FIG. 4B) produces magnification of the deflection applied to the linear knobs 62. Deflection (or travel, used interchangeably herein) of the third puller wire 35 can be determined using the following equations with reference to FIG. 5:

$$k=\text{sqrt}(R^2-h^2) \qquad \text{Eqn. (1)}$$

$$k'=\text{sqrt}(R'^2-h'^2) \qquad \text{Eqn. (2)}$$

$$T=L+k'-k \qquad \text{Eqn. (3)}$$

$$T=L+\text{sqrt}(R^2+L^2\tan^2\phi-h^2)-\text{sqrt}(R^2-h^2) \qquad \text{Eqn. (4)}$$

Figure 6:
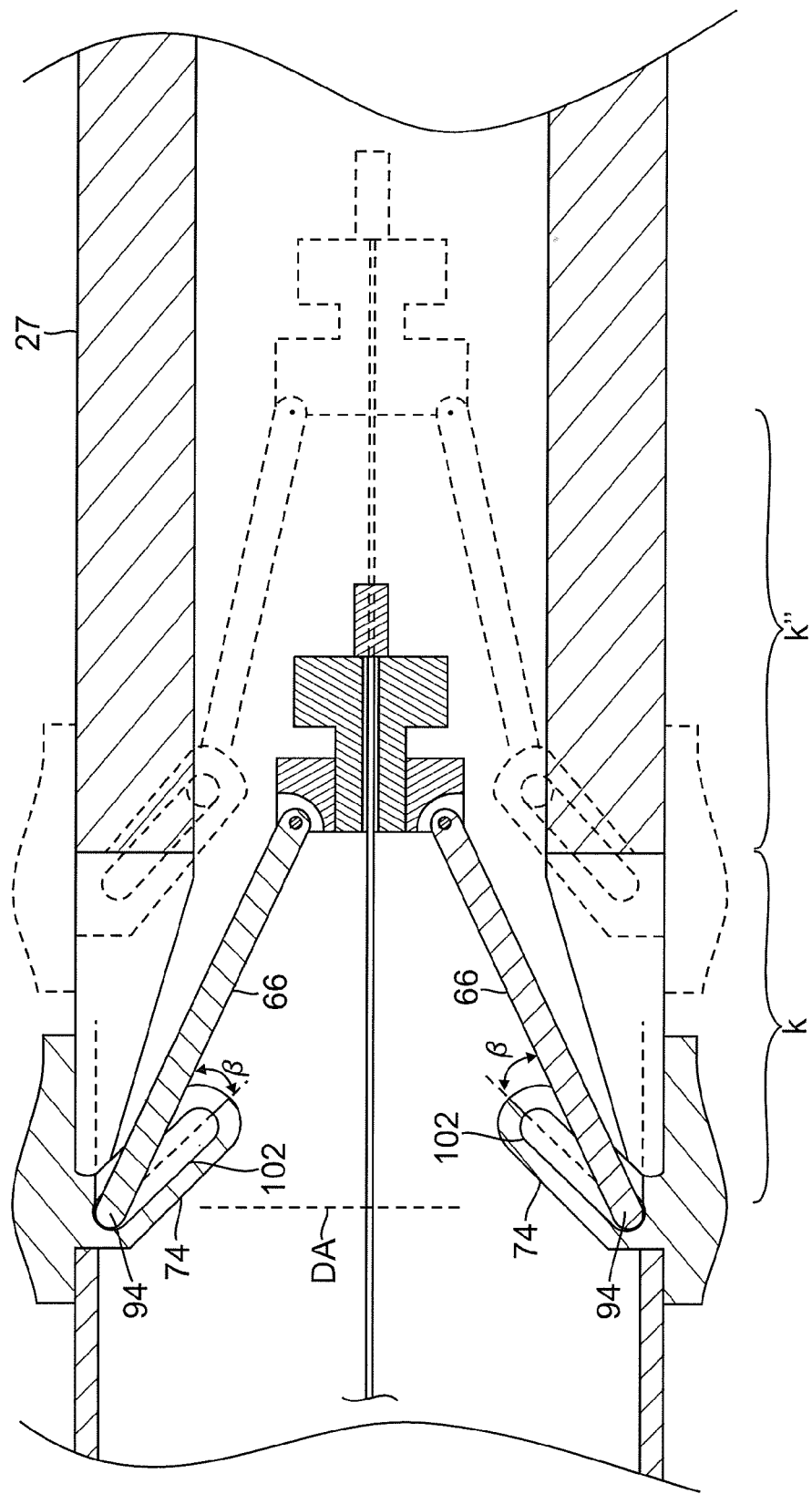
FIG. 6 is a side cross-sectional view of a first alternate embodiment of a linear motion actuator assembly.

Where
 h=maximum separation distance between inner wall of control handle housing and central longitudinal axis X
 h'=minimum separation distance between inner wall of control handle housing and central longitudinal axis X
 k=offset distance between finger and anchor at maximum separation distance (e.g., no travel of puller wire)
 k'=offset distance between finger and anchor at minimum separation distance (e.g., maximum travel of puller wire)
 L=maximum travel of linear knob
 R=length of arm
 φ=angle of incline
 T=final travel of puller wire The magnification of deflection can be increased by decreasing the angle β of the slot 102 relative to housing 27 as illustrated in FIG. 6. In contrast to the embodiment of FIG. 4, the offset distance k of the anchor 64 when the outer ends 94 of the arms 66 are at their maximum separate distance is the same, but the offset distance k" of the anchor in FIG. 5 is greater than the offset distance k' of FIG. 4.

Figure 7:
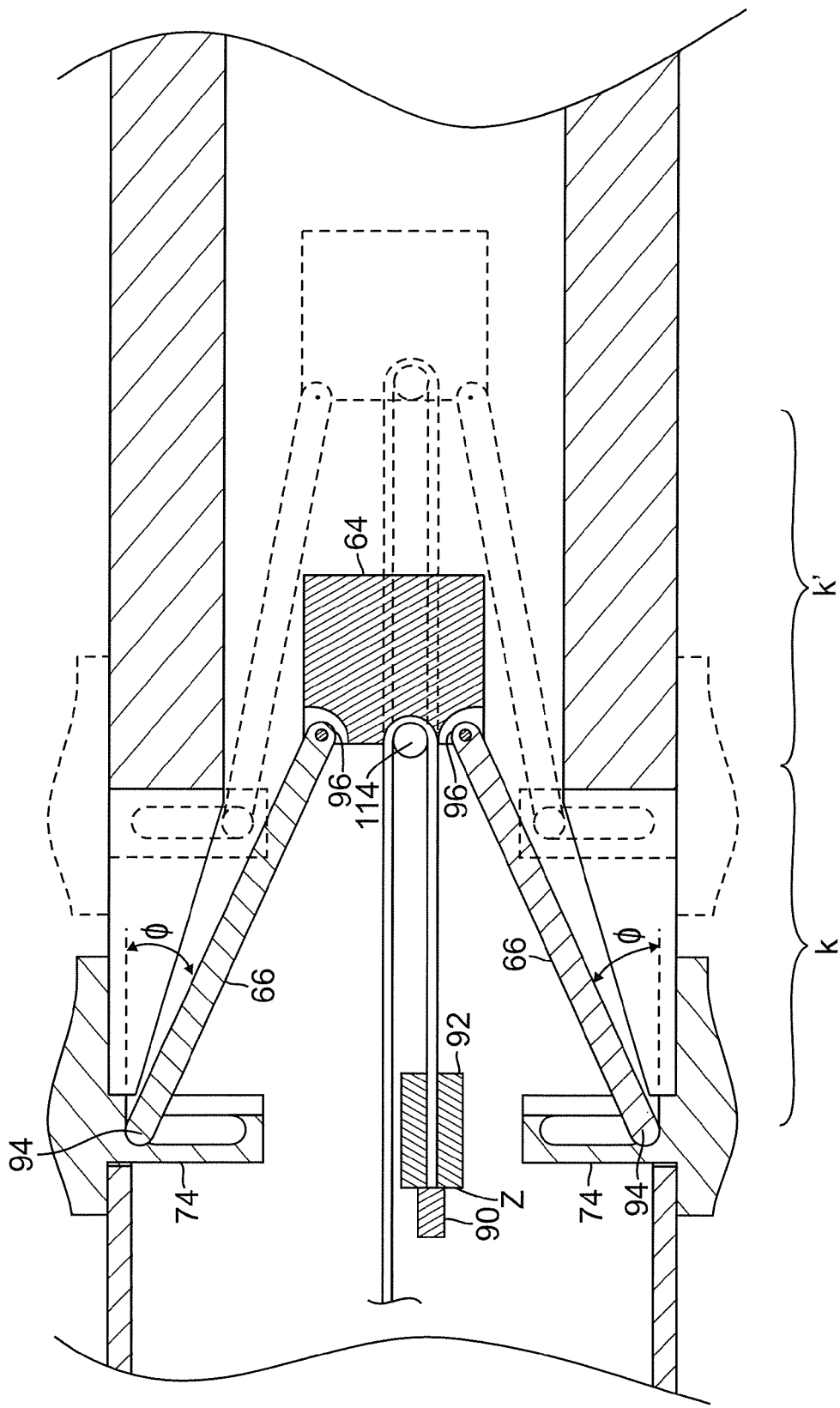
FIG. 7 is a side cross-sectional view of a second alternate embodiment of a linear motion actuator assembly.

The magnification of the deflection can be further increased by a factor of two by use of a pulley 114 on the anchor 64. With reference to FIG. 7, by wrapping the third puller wire 35 around the pulley 114 and anchoring the proximal end by fixing the ferrule 90 distal of the pulley, the travel distance of the puller wire 35 can be multiplied by a factor of two. Applying Equations (1)-(4) above, the multiplication factor X can be solved by the following equation:

$$X=1+\text{sqrt}((R^2-h^2)/L^2\tan^2\phi)-\text{sqrt}((R^2-h^2)/L^2) \qquad \text{Eqn. (5)}$$

Where the pulley 114 is used at a junction of the inner ends 96 of the arms 66 as illustrated in FIG. 7, the total travel $T_{pulley}$ and multiplication factor $X_{pulley}$ can be expressed as follows:

$$T_{pulley}=2L+2\text{sqrt}(R^2+L^2\tan^2\phi-h^2)-2\text{sqrt}(R^2-h^2) \qquad \text{Eqn. (6)}$$

$$X_{pulley}=2+2\text{sqrt}((R^2-h^2)/L^2+\tan^2\phi)-2\text{sqrt}((R^2-h^2)/L^2) \qquad \text{Eqn. (7)}$$

Figure 8:
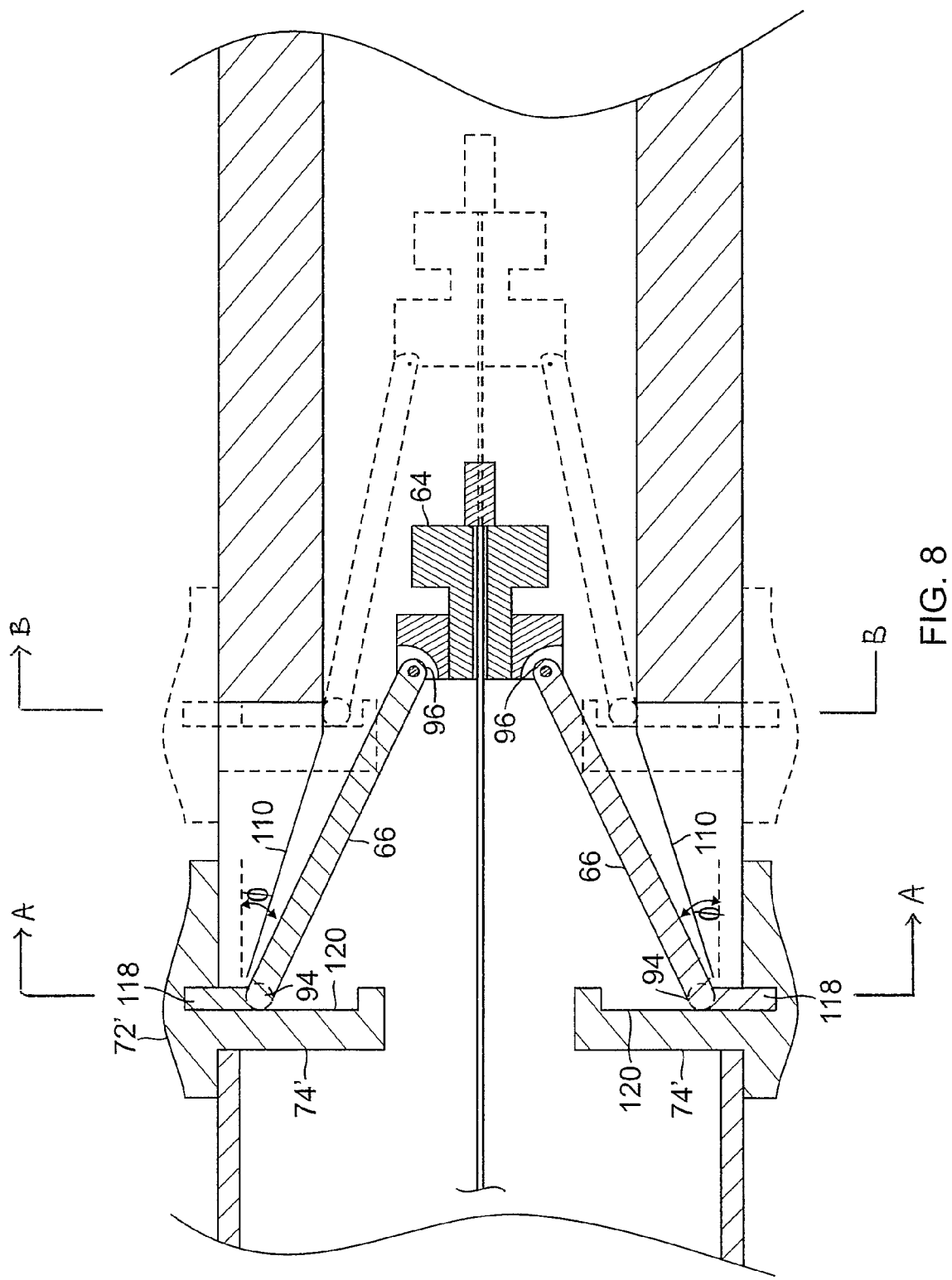
FIG. 8 is a side cross-sectional view of a third alternate embodiment of a linear motion actuator assembly.
Figure 8A:
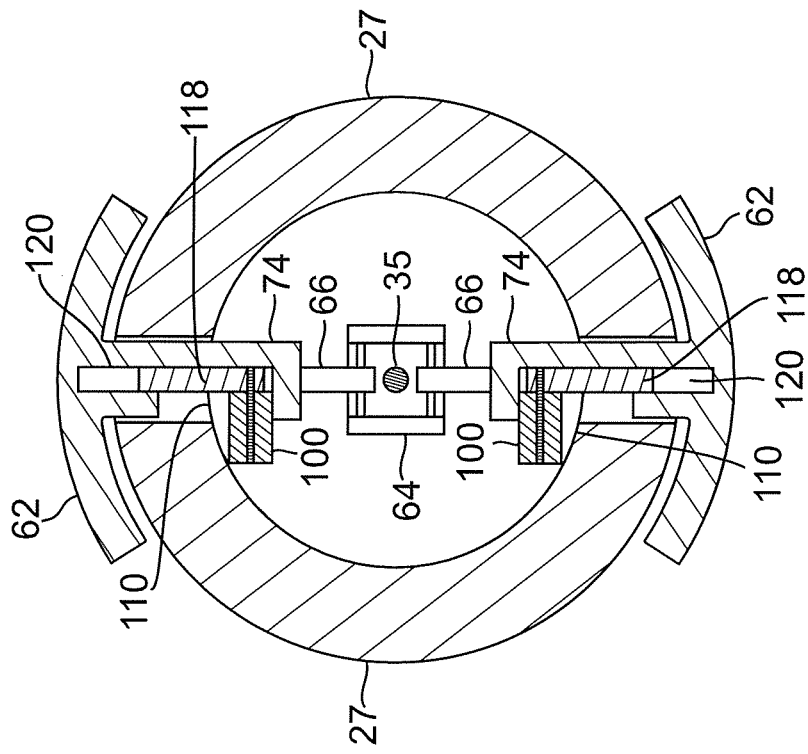
FIG. 8A is an end cross-sectional view of the linear motion actuator assembly of FIG. 8, taken along line A-A.
Figure 8B:
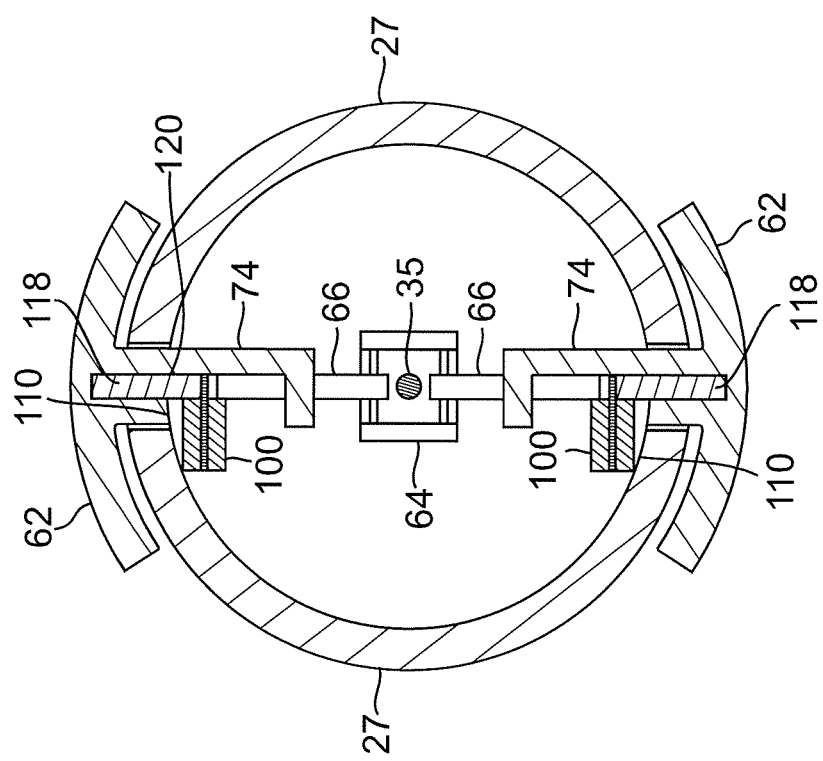
FIG. 8B is an end cross-sectional view of the linear motion actuator assembly of FIG. 8, taken along line B-B.

In another embodiment as illustrated in FIGS. 8, 8A and 8B, each outer end 94 has an extension 118 that is received in an elongated channel 120 formed along the length of finger 74' of knob 62'. The channel 120 runs the length of the finger and into the outer portion 72 of the knob 62' so that the extension 118 slides along the channel 120 as the outer end 94 moves relative to the finger and the roller 100 rides on the incline 110. The variable connection between the extension 118 and the finger 74' is variable so as to allow the angle β of the arm 66 to vary for magnifying the travel of the third puller wire 35. The variable connection may be by accomplished by use of a flexible, deformable and/or elastic material for the construction of the finger and extension, or a hinge between the finger and extension. The connection may be biased, e.g., by a leaf spring, toward a smaller angle (versus a larger angle) between the extension 118 and the arm 66. In any case, the rollers 100 are provided to follow the incline 110 in magnifying the deflection as described above.

Figure 9:
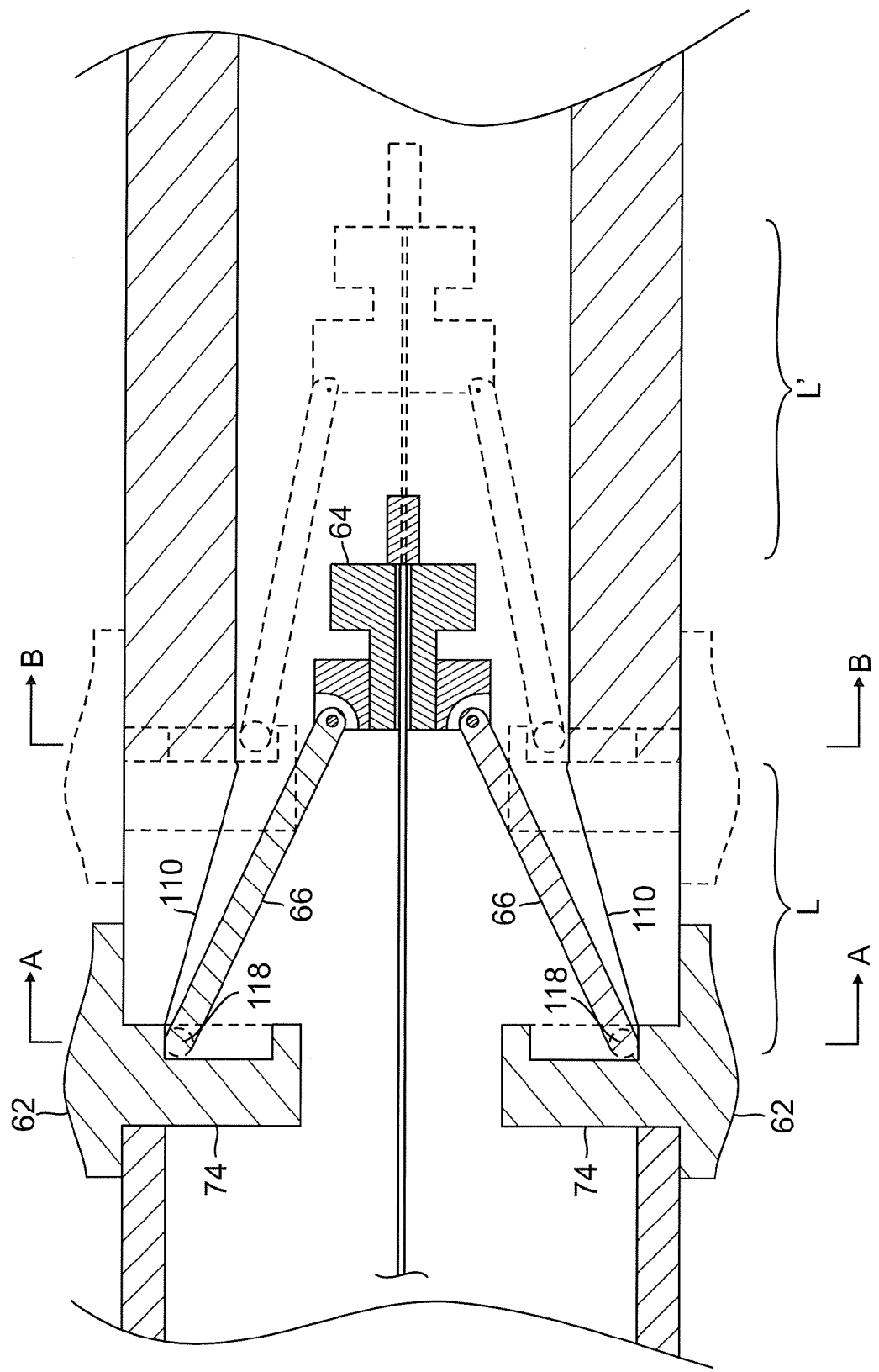
FIG. 9 is a side cross-sectional view of a fourth alternate embodiment of a linear motion actuator assembly.
Figure 9B:
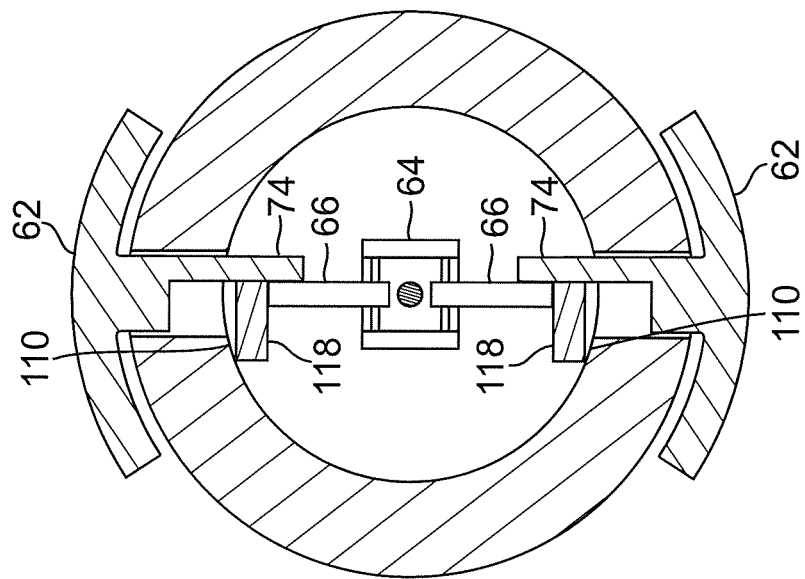
FIG. 9B is an end cross-sectional view of the linear motion actuator assembly of FIG. 9, taken along line B-B.
Figure 9A:
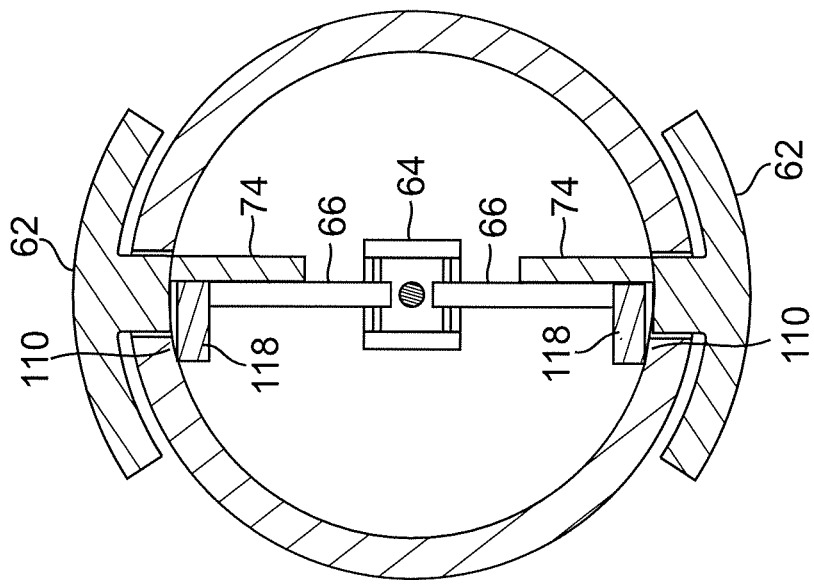
FIG. 9A is an end cross-sectional view of the linear motion actuator assembly of FIG. 9, taken along line A-A.

In another alternative embodiment as shown in FIGS. 9A, 9B, the extension 118 extends transversely from the outer end 94 of the arms (e.g., into the page in FIG. 9) so that the extension is supported on the incline 110.

In use, a suitable guiding sheath is inserted into the patient with its distal end positioned at a desired mapping location. An example of a suitable guiding sheath for use in connection with the present invention is the Preface™. Braiding Guiding Sheath, commercially available from Biosense Webster, Inc. (Diamond Bar, Calif.). The distal end of the sheath is guided into one of the chamber, for example, the atria. A catheter in accordance with the present invention is fed through the guiding sheath until its distal end extends out of the distal end of the guiding sheath. As the catheter is fed through the guiding sheath, the distal assembly 17 is straightened to fit through the sheath. Once the distal end of the catheter is positioned at the desired location, the guiding sheath is pulled proximally, allowing the deflectable intermediate section 14 and distal assembly 17 to extend outside the sheath, and the distal assembly 17 returns to its original shape due to its shape-memory.

By manipulating and rotating the deflection dial 50 to deflect the intermediate section 14, the distal assembly 17 is then inserted into a pulmonary vein or other tubular region (such as the superior vena cava, or inferior vena cava) so that the outer circumference of the generally circular main region 39 of the assembly 17 is in contact with a circumference inside the tubular region. Turning the deflection dial 50 in one direction deflects the intermediate section 14 to that direction. Turning the deflection 50 in the opposite direction deflects the intermediate section 14 to that opposite direction. Tension of the deflection dial 50 is adjusted by manipulating and rotating a tension dial 51. Turning the dial 51 in one direction increases the tension. Turning the dial 51 in the opposition direction decreases the tension.

The circular arrangement of the electrodes on the generally circular portion 39 permits measurement of the electrical activity at that circumference of the tubular structure so that ectopic beats between the electrodes can be identified. The size of the generally circular main region 39 permits measurement of electrical activity along a diameter of a pulmonary vein or other tubular structure of or near the heart because the circular main region has a diameter generally corresponding to that of a pulmonary vein or other tubular structure. By manipulating the linear knobs 62, the assembly 17, in particular, the generally circular main region 39, is adjusted to fit the pulmonary vein or other tubular structure. In the disclosed embodiment, by drawing proximally on the knobs 62, the contraction wire 35 is drawn proximally to tighten and decrease the diameter of the generally circular region 39. By pushing forward on the knobs 62, the contraction wire 35 is pushed distally to release the generally circular region 39 and expands its diameter. Preferably at least about 50%, more preferably at least about 70%, and still more preferably at least about 80% of the circumference of the generally circular main region is in contact with a circumference inside the tubular region.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. For example, the catheter can be adapted such that the third puller wire advances and retracts another component such as a guide wire or a needle. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A control handle for a medical device having an elongated body, a distal assembly distal the elongated body, the distal assembly having an adjustable configuration, the medical device further comprising a puller member extending through the elongated body and the distal assembly, the control handle comprising:
   a housing configured with a first incline and a second incline;
   an actuator assembly comprising:
      first and second knobs jointly movable for a predetermined distance relative to the housing;
      a body to which a proximal end of the puller member is fixed;
      a first arm extending between the first knob and the body, the first arm having an outer end coupled to the first knob and an inner end coupled to the body; and
      a second arm extending between the second knob and the body, the second arm having an outer end coupled to the second knob and an inner end coupled to the body,
   wherein the body is movably suspended by the first and second arms, and the first and second knobs actuate the outer ends of the first and second arms to move along the first and second inclines in varying a separation distance between the outer ends so that the puller wire travels a greater distance than the predetermined distance for adjusting the configuration of the distal assembly.

2. A control handle of claim 1, wherein each of the first and second inclines is formed from a portion of the housing with a maximum thickness at one end of the portion and a minimum thickness at the other end of the portion.

3. A control handle of claim 2, wherein the separation distance decreases as the first and second knobs actuate the outer ends of the first and second arms to move along the first and second inclines from the minimum thickness to the maximum thickness.

4. A control handle of claim 1, wherein the first and second knobs are generally diametrically opposed from each other on the housing.

5. A control handle of claim 1, wherein each first and second knobs has an outer portion and an inner portion, the outer ends of the first and second arms being movably coupled to the inner portion.

6. A control handle of claim 1, wherein the first and second arms are generally rigid.

7. A control handle of claim 1, wherein the body is movable along a longitudinal axis of the housing.

8. A control handle of claim 5, wherein each inner portion extends through a respective axial slot formed in the housing.

9. A control handle of claim 5, wherein each outer end is movably coupled to a slot formed in a respective inner portion.

10. A control handle of claim 9, wherein each outer end is adapted to vary at least its position relative to the slot.

11. A control handle of claim 9, wherein each outer end is adapted to vary at least its angle relative to the slot.

12. A catheter comprising:
   an elongated body;
   a distal assembly having an adjustable configuration;
   a puller wire extending through the elongated body and the distal assembly;

a control handle comprising:
  a housing configured with a first incline and a second incline;
  a linear motion actuator assembly, comprising:
    a first knob and a second knob each movable for a predetermined distance relative to the housing, respectively;
    a body to which a proximal end of the puller wire is fixed;
    a first arm extending between the first knob and the body, the first arm having an outer end movably coupled to the first knob and an inner end movably coupled to the body; and
    a second arm extending between the second knob and the body, the second arm having an outer end movably coupled to the second knob and an inner end movably coupled to the body,
wherein the body is movably suspended by the first and second arms, and the first and second knobs actuate the outer ends of the first and second arms to move along the first and second inclines in varying a separation distance between the outer ends for moving the puller wire a greater distance than the predetermined distance for adjusting the configuration of the distal assembly.

13. A catheter of claim 12, further comprising a pair of puller members extending from the control handle to at or near a distal end of the elongated body, wherein the control handle further comprises a deflection assembly adapted to act on the pair of puller members.

14. A catheter of claim 12, wherein the distal assembly has a generally circular distal portion and a generally straight proximal portion, wherein adjustment of the puller member varies the generally circular distal portion.

15. A catheter of claim 12, wherein the first and second knobs are adapted to move linearly in a longitudinal direction relative to the control handle.

16. A catheter of claim 12, wherein the first and second arms have inner ends that are pivotally connected to the body and outer ends that are pivotally connected to the first and second knobs, respectively.

17. A catheter of claim 12, wherein the body includes a pulley that engages the puller member.

* * * * *